United States Patent [19]

Latulippe et al.

[11] Patent Number: 5,394,983
[45] Date of Patent: Mar. 7, 1995

[54] STERILIZATION BLOCK WITH SLIDING LID AND COOPERATING GRAPHICS

[75] Inventors: Michael Latulippe, Derry; John A. Brooks, Londonderry, both of N.H.

[73] Assignee: Poly-Vac, Inc., Manchester, N.H.

[21] Appl. No.: 960,986

[22] Filed: Oct. 14, 1992

[51] Int. Cl.⁶ .......................... B65D 83/10; B65D 1/36
[52] U.S. Cl. ................................... 206/370; 206/438; 206/459.5; 206/562; 206/564
[58] Field of Search ............... 206/363, 364, 369, 370, 206/438, 562–564, 569–572, 459.5

[56] References Cited

U.S. PATENT DOCUMENTS

| | | | |
|---|---|---|---|
| 2,895,602 | 7/1959 | Hait | 206/564 X |
| 3,122,265 | 2/1964 | Innis | 206/564 X |
| 3,300,055 | 1/1967 | Rohr | 206/564 X |
| 3,349,937 | 10/1967 | Duff et al. | 206/305 X |
| 3,743,088 | 7/1973 | Henkin | 206/569 |
| 4,153,160 | 5/1979 | Leigh | 206/370 |
| 4,195,059 | 3/1980 | Whitcher et al. | 206/569 X |
| 4,195,734 | 4/1980 | Boner et al. | 206/562 X |
| 4,898,276 | 2/1990 | Georgakis | 206/369 |

FOREIGN PATENT DOCUMENTS

| | | | |
|---|---|---|---|
| 1024588 | 1/1953 | France | 206/369 |
| 4072167 | 3/1992 | Japan | 206/564 |

Primary Examiner—Bryon P. Gehman
Attorney, Agent, or Firm—Eugene E. Renz, Jr.

[57] ABSTRACT

A device for use in a surgical delivery system, comprising a block formed from a sterilizable plastic and having a plurality of cavities with drain holes or vents. The cavities are sized and shaped to display a plurality of surgical components. A lid slideably engages the block and is sized to enclose the cavities when the lid is in a closed position. The block includes lid guides for positioning the lid in the closed position. Printed indicia for displaying graphics with the block are non-removably mounted in the block in a position for displaying the block graphics upon removal of the lid. The lid includes lid graphics displaying at least a portion of the contents of the cavities. An angularly disposed slot in the block along one side thereof is used to display the lid graphics in cooperation with the contents in the cavities.

8 Claims, 4 Drawing Sheets

STERILIZATION BLOCK WITH SLIDING LID AND COOPERATING GRAPHICS

FIELD OF THE INVENTION

The present invention relates to a surgical delivery system block having a sliding lid. More particularly, the invention relates to a block for containing a plurality of surgical elements arranged in a surgical delivery system, in which the elements of the surgical delivery system are contained in individual cavities, with the arrangement of the cavities being combined with graphics to instructively display the surgical elements in a systematic manner.

BACKGROUND OF THE INVENTION

As surgical procedures have evolved over the centuries, efforts have been made to systemize surgical procedures so that all of the instruments needed for a particular surgical procedure are available in the operating room in a sterile and usable condition. In early years, a sterilizing device has been employed to sterilize generic surgical instruments which are then selected by the operating team for particular needs of the planned surgery. One can easily envision a plurality of instruments arranged in an appropriate manner on trays or towels for use during surgery.

For simple surgery, this simple method of laying out the instruments is adequate. However, as surgical procedures become more complex, and as small and more intricate surgical components are employed, it has become more and more difficult to provide an effective surgical delivery system for delivering the appropriate surgical components in the proper sequence. Efforts have been made to enclose multiple surgical components in containers. However, no successful surgical delivery system has been developed at this time.

Sensitive surgical instruments and a multiplicity of small surgical components cannot be placed haphazardly in a container for several reasons. The sensitive surgical instruments must not be blunted or scratched. Scalpels, clamps, and other instruments must function with the precision and sensitivity for which they have been designed. Surgical components such as pins, plates, screws and the like often time are presented in a plurality of sizes and shapes. Surgical procedures cannot wait for someone to sort through a quantity of bone screws, for example, looking for the right size and/or shape for the next step in the surgical procedure.

In addition, the containers which might be usable for a surgical delivery system must be capable of withstanding sterilization. In prior systems, plastics were discarded and metal containers were used since metals such as stainless steel and aluminum are capable of withstanding sterilization conditions. However, use of titanium and other metals in surgical elements give rise to an electro-chemical reaction with stainless steel, thereby prohibiting the co-mingling of those two metals. In addition, efforts to use high temperature polymers have not met with success because these high temperature polymers typically are not receptive to printing so that inks won't adhere to the surfaces of the high temperature polymers.

Accordingly, it is an object of this invention to provide a device for use in a surgical delivery system in which devices can be sterilized.

More specifically, it is an object of this invention to provide a delivery system which is sterilizable by steam auto-clave, dry heat (flash) to 320° F., ethylene oxide sterilization, gamma radiation, cold sterilants, or disinfectants and germicides.

Another object of the present invention is to provide such a device which will not blunt or scratch sensitive surgical instruments.

Yet another object of the present invention is to provide a device which permits systematic arrangement of surgical components such as plates, screws and the like in individual locations and in a pattern which is suitable for a surgical procedure.

Still another object of the present invention is to provide a device for use in surgical delivery systems which includes graphic information which is presented during the surgical procedure in a manner which cooperatively displays the graphics in cooperation with the surgical elements contained in the container.

Other objects will appear hereinafter.

SUMMARY OF THE INVENTION

It has now been discovered that the above and other objects of the present invention may be accomplished in the following manner. Specifically, a device is provided in accordance with the present invention for use in a surgical delivery system.

The device comprises a block which is formed from a sterilizable plastic and which has a plurality of cavities, those cavities being sized and shaped to display a plurality of surgical components. Also included is a lid which slideably engages the block and which is sized to enclose the cavities in the block when the lid is in a closed position. The block includes guides to position the lid over the cavities. In addition, printed indicia means are also provided for displaying desired graphics in the block itself. The graphics are non-removably mounted in the block in a position for display of the block graphics upon removal of the lid.

Surgical components particularly for plastic surgery or bone reconstruction surgery, may include a plurality of plates of predetermined sizes and shapes. The surgical components will often also include a plurality of screws which are sized to mount the plates during the surgical procedure. The cavities in the block are arranged so that the selection of the components is systemized in accordance with the particular procedure being performed.

In a preferred embodiment, the lid also includes lid graphics which display at least a portion of the contents of the cavities. In this embodiment, an angularly disposed slot is formed in the block along one side for displaying the lid graphics in cooperation with the cavities.

In order to preserve the integrity of the container, detente means are provided for holding the lid in the closed position to prevent inadvertent movement of the lid to expose the contents of the cavities.

BRIEF DESCRIPTION OF THE DRAWINGS

These and other objects of the present invention and the various features and details of the operation and construction thereof are hereinafter more fully set forth with reference to the accompanying drawings, where.

DETAILED DESCRIPTION OF THE PREFERRED EMBODIMENT

Figure 1:
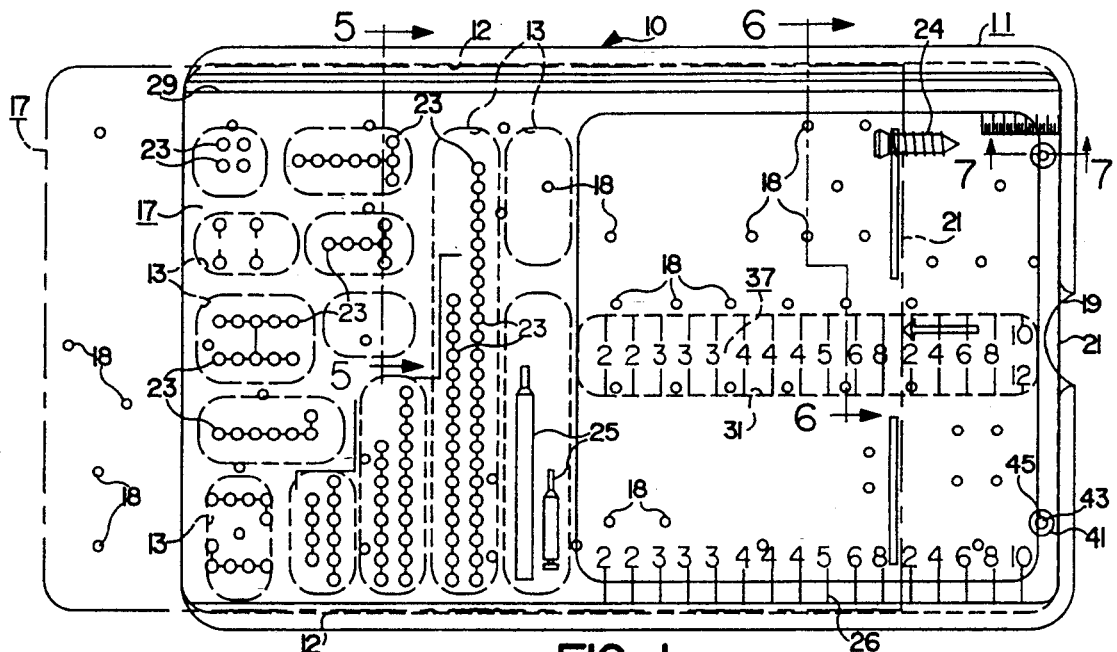
FIG. 1 is a plan view of a sterilization block device according to the present invention, with a sliding lid shown in a closed position in full line and in a partially open position in dot and dash outline.
Figure 2:
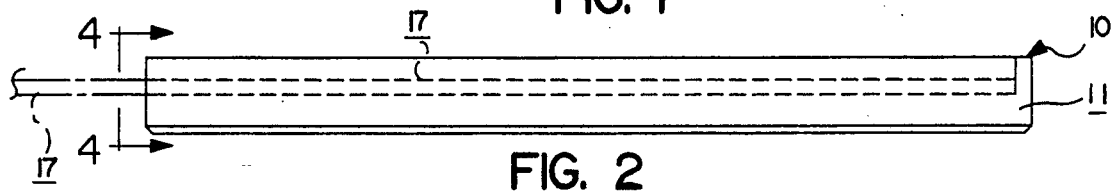
FIG. 2 is a side elevational view of FIG. 1.

A device according to the present invention, shown generally by reference numeral 10, is illustrated in FIG. 1. The device includes a sterilization block 11 with a plurality of cavities 13 which in turn have drain holes 15 which function as will be described hereinafter.

Covering and fixedly spaced above the cavities 13 is a transparent lid 17, shown in closed position in full line in FIG. 1 and in a partially open position in dot and dash outline. The transparent lid 17 is mounted for slidable openings or closing from one side only. To this end the two sided edges of the lid 17 are contained within two coextending slots 12 in the side walls of the sterilization block 11. The lid 17 lower or inner face is positioned by the slots 12 to lie slightly above the upper face of cavities 13 and screw pocket cavity as shown clearly in FIGS. 5, 6, and 7. With reference to FIG. 1, when in a closed position the right hand edge of the lid abuts against an end wall ridge formed on the sterilization block and is retained in this closed position by means of the spring biased balls 43 engaging in corresponding holes 45 along the right hand edge of lid 17. When in the closed position the lids left hand edge is planar with the left hand edge of the sterilization block 11.

Lid 17 also includes a plurality of vent or drain holes 18. Block 11 includes an arcuate cut out 19 which permits pressure to be applied to the trailing edge 21 of lid 17, so that the lid will extend out to partially open position, thereby allowing the lid 17 to be grasped along its extending edge and removed as desired.

Figure 8:
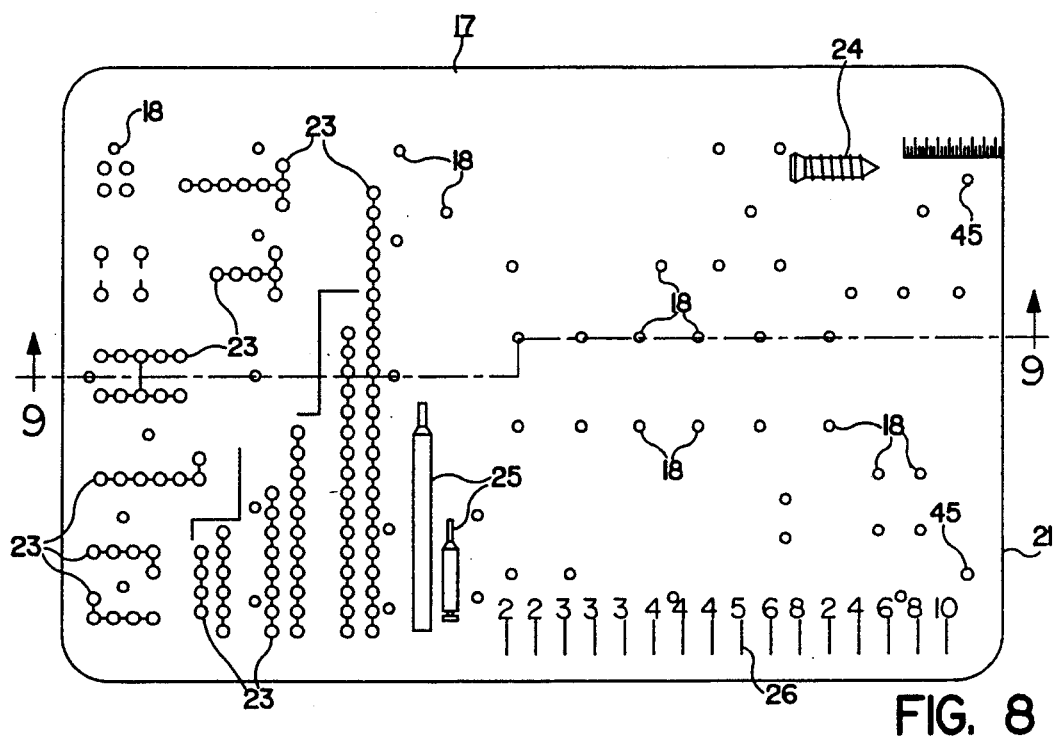
FIG. 8 is plan view of the sliding lid.
Figure 9:
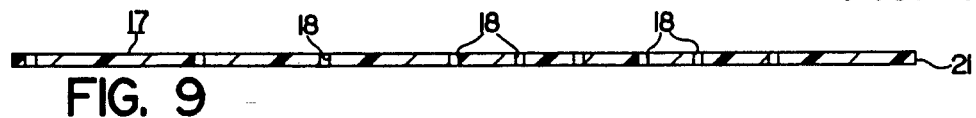
FIG. 9 is a sectional elevational view taken along the line 9,9 of FIG. 8.

Lid 17 also includes a plurality of graphic indicia which depict the particular surgical components which are contained in the underlying cavities 13. As noted on FIG. 1, the lid 17 has printed on its surface a plurality of maxillofacial surgical elements of various sizes and configurations. These graphics correspond to the actual surgical components which are placed in the cavities. As will be appreciated herein below, the graphical representation of the contents is of significant importance during the surgical procedure. To this end shown graphically as indicia on the lid are various surgical tools such as plates 23, screws 24 and micro drills 25. There is in addition a printed scale 26 of ascending order locating rows of screws according to length in millimeters. In order to quickly locate the particular screws which are needed for the surgical procedure being conveyed by the device of this invention. These lid graphics are best shown in FIG. 8 where maxillofacial plates 23, screw 24, drills 25 and other related graphic information 26 are shown printed on the upward face of lid 17.

Figure 3:
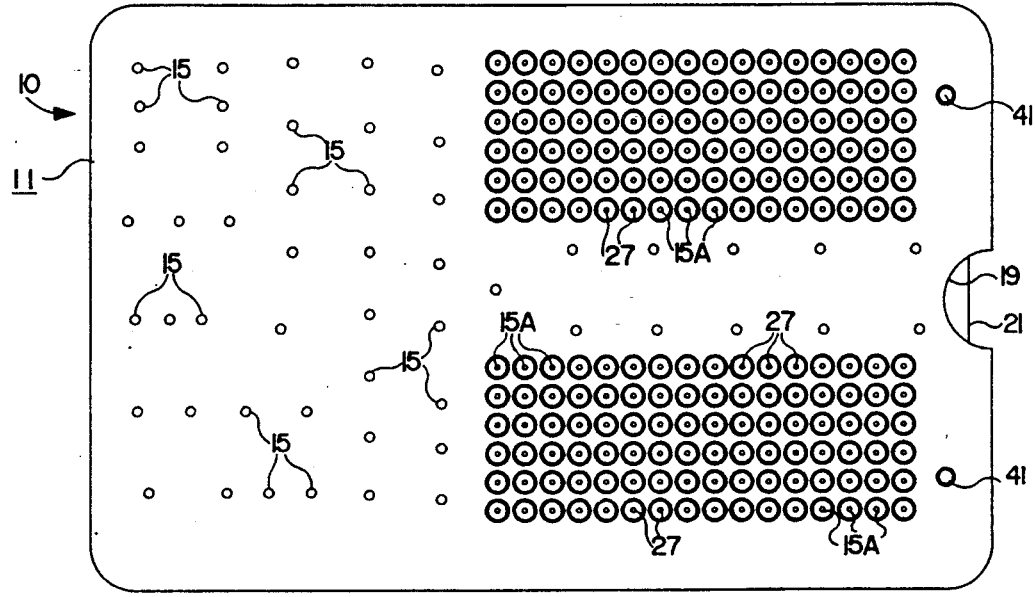
FIG. 3 is a bottom plan view of FIG. 2.
Figure 5:
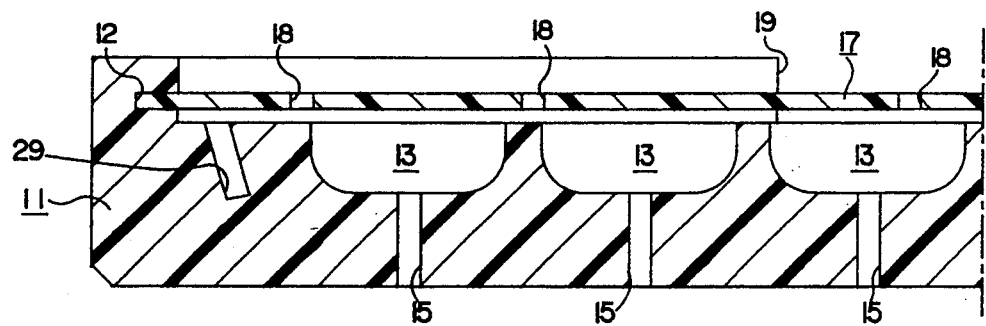
FIG. 5 is an enlarged, fragmentary, sectional elevational view taken along the line 5,5 of FIG. 1.
Figure 6:
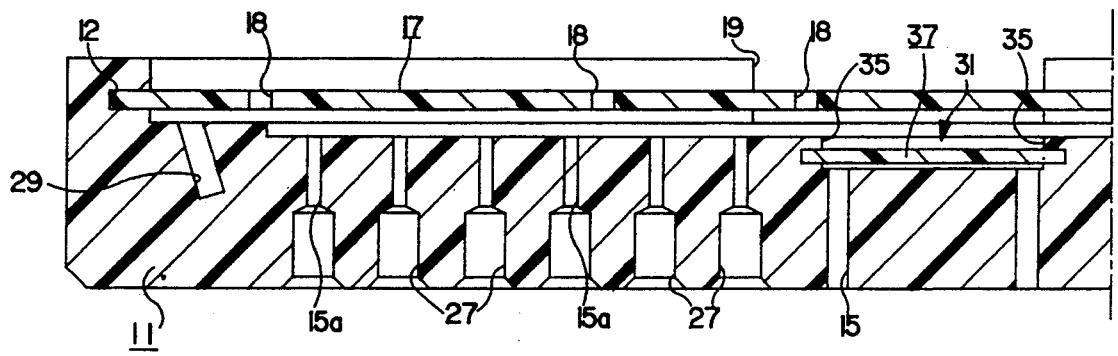
FIG. 6 is an enlarged, fragmentary, sectional elevational view taken along the line 6,6 of FIG. 1.

FIG. 3 shows the bottom of block 11, illustrating drain holes 15 and opening into the bottom cavities 13. Larger holes 27 extend approximately mid-way up from the bottom of block 11 to axially intersect the very small diameter screw pockets 15A. Turning first to FIG. 5, shown greatly enlarged, the relationship between the block 11, cavity 13, drain hole 15 and lid 17 can be seen, along with vent hole 18 in the lid 17. In FIG. 6 these same relationships are shown between the block 11, the screw pocket holes 15A which are use for storing screws and the larger diameter ports 27. Large ports 27 serve to permit increased sterilization of the small screw pocket 15A holes to which they are axially aligned.

Figure 4:
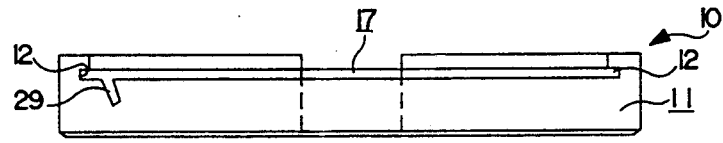
FIG. 4 is an end elevational view of the device taken along the line 4,4 of FIG. 2.

Extending along the entire length of the block 11 is an angular disposed slot 29 shown in FIGS. 4, 5 and 6. This permits the lid 17 to be placed in a display orientation shown in FIG. 12, As noted in FIG. 12 the various graphic information is shown on the surface of lid 17, previously described, and again corresponds to the location of the actual element in the cavities 13 and screw retaining holes 15A.

Figure 10:
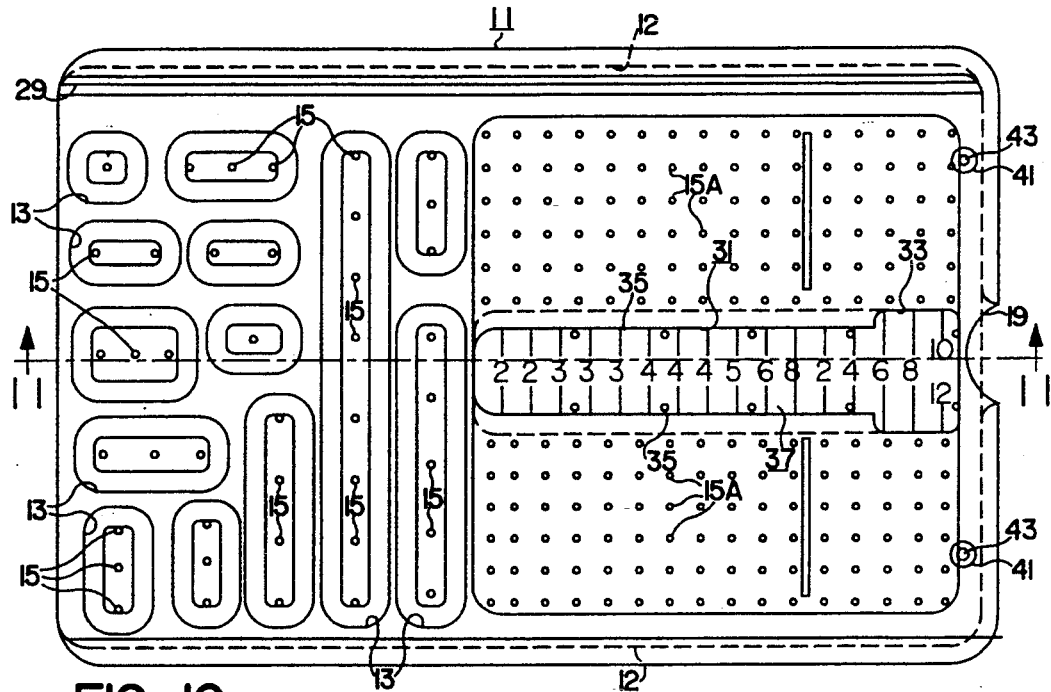
FIG. 10 is a plan view of the device of the present invention with the sliding lid removed.

Turning now to FIG. 10 certain additional features of the device of this invention are shown. Specifically, the actual orientation of the cavities 13 in block 11 can be seen. The multiplicity of screw holes 15A illustrate the large number of screws which can be contained in this device.

Figure 11:
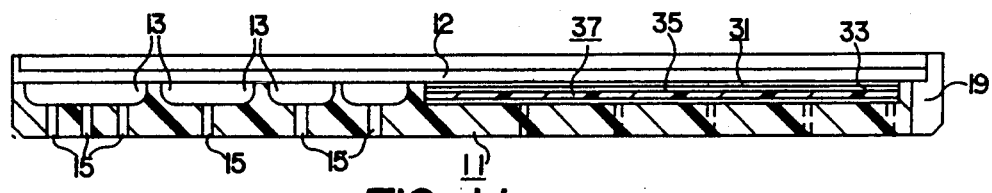
FIG. 11 is a sectional elevational view taken along the line 11,11 of FIG. 10.

The block 11 also includes an elongated cavity 31 which has an enlarged portion 33 and a narrower portion which defines a lip 35 extending inward to face a corresponding lip 35 on the other side of the elongated cavity 31. A flexible print receptive plate 37 is provided with graphics which are to remain in the block 11 after the lid 17 has been removed. Flexible print receptive plate 37 is sized to have essentially the same width as the enlarged portion 33 of elongated cavity 31, and to have a length substantially equal to the length of cavity 31. The flexible print receptive plate 37 may be inserted through the enlarge portion 33 of cavity 31 so that the sides of plate 37 fit under the extending lip 35 on each side. Because the length of the plate 37 is substantially the same as the length of the cavity as can be seen in FIG. 11, the plate 37 will fit down into cavity 31 and will not be removable under most circumstances. The lip 35 extends over the plate 37, as shown in perspective in FIG. 12, and there is no convenient way to remove plate 37 from cavity 31.

Figure 12:
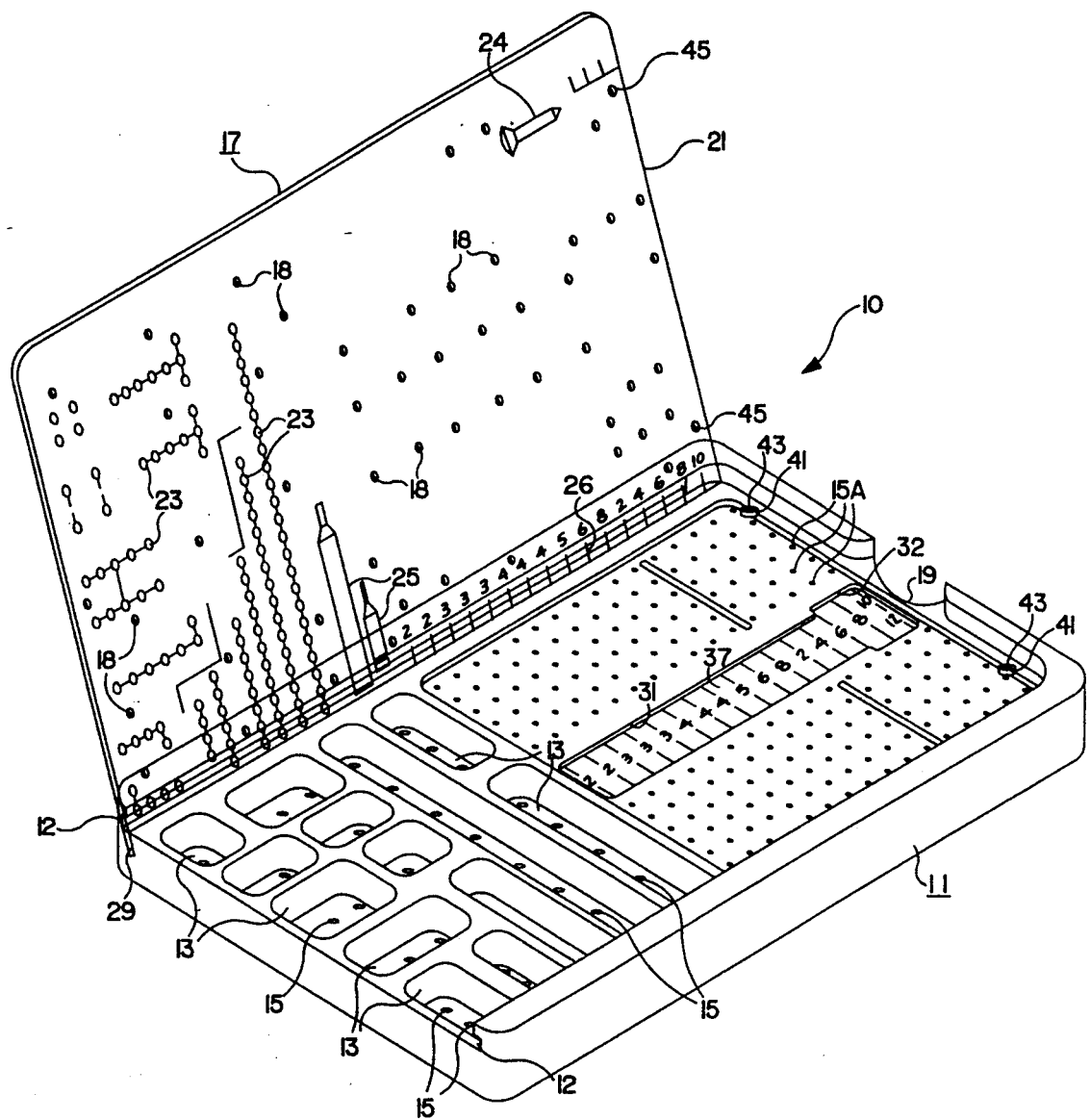
FIG. 12 is an isometric view showing the block and slidable lid during use.

As previously mentioned FIG. 1 illustrates the lid and block in a closed position. FIG. 12 illustrates the lid 17 which has been removed from the block 11 and placed in angular disposed slot 29 to display the graphics in a way that corresponds to the components kept in screw pocket holes 15A and cavities 13.

Figure 7:
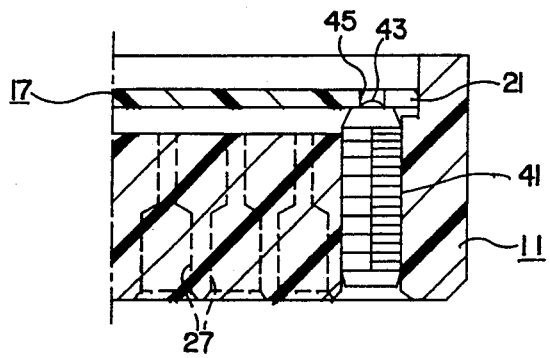
FIG. 7 is an enlarged, fragmentary, sectional elevational view taken along the line 7,7 of FIG. 1.

The device of this invention is intended to be sterilized under any of the conventional sterilization procedures. It is essential that the lid remain fixedly on the block 11 and spaced above the cavities of pockets until that time when opening the cavity is desired, such as by use of the arcuate cutout 19. FIG. 7 illustrates in an enlarged fragmentary sectional elevational view the details of the retaining means which keeps lid 17 in a closed position on block 11. The retaining means comprises a threaded cylinder 41 containing a spring biased ball 43. The cylinder 41 is positionally screwed into holes 41 in the block 11 which are aligned to correspond to the holes 45 in lid 17. Thus, when the lid is fully closed and in the position shown in FIG. 1, the spring biased balls 43 extend into holes 45. This spring bias can be overcome by pressure intentionally placed on the trailing edge 21 of lid 17, through arcuate cutout 19 and the lid can be removed for placement as shown in FIG. 12. However, during sterilization, shipment, and other activities up until the time when the lid is to be removed, the spring biased balls 43 engaged in holes 45 of the lid 17 to sufficiently to prevent inadvertent removal of the lid.

As previously noted, the device of this invention is 100% sterilizable. Steam autoclave, drive heat or flash up to 320° F., ethylene oxide sterilization, gamma radiation, cold sterilants, or disinfectants or germicides may all be employed to provide a product which is suitable for use in the operating room or other intended environment. Preferred materials for the block itself are various high density polymers such as acetyl copolymers, acetyl homopolymers, high density polypropylene, tetrafluoroethylene, and the like. The lid 17 and flexible print receptive plate 37 are made from materials to which printed matter will adhere ever during the sterilization processes. Preferred lid materials are poly ether imides and poly aryl ethers.

Another advantage of the present invention is the absence of any metallic contact between the fragile surgical elements and the containing and retaining means. Stainless steel and titanium are not allowed to be in contact with each other and this chemical reaction and others which potentially can take place during sterilization or over long periods of contact have been eliminated.

Use of the present invention is capable of improving the accuracy and thoroughness of surgical procedures as well as decreasing the amount of time necessary for completing a repetitive series of surgical procedures using a plurality of surgical elements, such as the maxillofacial plates as illustrated.

Other modifications and additional embodiments will be approved to those skilled in the art upon a reading of the description of this invention. While particular embodiments of the present invention have been illustrated and described as it is not intended to limit the invention, except as defined by the following claims.

What is claimed is:

1. A device for use in surgical delivery system, comprising:
    a block formed from sterilizable plastic and having a plurality of cavities, said cavities being sized and shaped to display a plurality of surgical components;
    a removable lid having lid graphics thereon and slideably engaging said block and sized to enclose said cavities in a closed position, said block including lid guides for positioning said lid in said closed position;
    indicia means for displaying block graphics printed thereon, said indicia means being fixedly mounted in said block in a position for displaying said block graphics upon removal of said lid; and
    lid mounting means in said block for mounting said lid in an open position for displaying said lid graphics in cooperation with said cavities.

2. The device of claim 1 wherein said cavities include vent holes.

3. The device of claim 1 which further includes detent means for holding said lid in said closed position to prevent inadvertent movement of said lid to expose said cavities.

4. The device of claim 1 wherein said printed indicia means comprising a flexible print receptive plate and said block includes slot means for fixedly receiving said plate.

5. A device for use in surgical delivery system, comprising:
    a block formed from a sterilizable plastic and having a plurality of cavities with vent holds, said cavities being sized and shaped to display a plurality of surgical components;
    a removable lid having lid graphics thereon slideably engaging said block and sized to enclose said cavities in a closed position, said block including lid guides for positioning said lid in said closed position; indicia means for displaying block graphics printed thereon, said indicia
    means being fixedly mounted in said block in a position for displaying said block graphics upon removal of said lid, said lid graphics displaying at least a portion of the contents of said cavities; and
    angularly disposed slot means in said block along one side thereon for mounting said lid in a position for displaying said lid graphics in cooperation with said cavities.

6. The device of claim 5 which further includes detent means for holding said lid in said closed position to prevent inadvertent movement of said lid to expose said cavities.

7. The device of claim 5 wherein said indicia means comprising a flexible print receptive plate and said block includes slot means for fixedly receiving said plate.

8. A device for use in a surgical delivery system, comprising:
    a block formed from sterilizable plastic and having a plurality of cavities, said cavities being sized and shaped to display a plurality of surgical components;
    a removable lid having graphics thereon slideably engaging said block and sized to enclose said cavities in a closed position, said block including lid guides for positioning said lid in said closed position; and
    lid mounting means in said block for mounting said lid in an open position for displaying said lid graphics in cooperation with said cavities.

* * * * *